United States Patent [19]

Bowen

[11] Patent Number: 4,997,427
[45] Date of Patent: Mar. 5, 1991

[54] EXTERNAL MALE URINARY CATHETER

[76] Inventor: Thomas M. Bowen, 13745 S.W. 79th Ct., Miami, Fla. 33158

[21] Appl. No.: 431,192

[22] Filed: Nov. 3, 1989

[51] Int. Cl.⁵ .............................................. A61F 5/44
[52] U.S. Cl. ...................................... 604/349; 604/353
[58] Field of Search .......................... 604/317, 345–353

[56] References Cited

U.S. PATENT DOCUMENTS

| | | | |
|---|---|---|---|
| 919,875 | 4/1909 | Johnson | 604/353 |
| 1,105,488 | 7/1914 | Clare | 604/353 |
| 1,228,452 | 6/1917 | Lawrence | 604/353 |
| 1,229,423 | 6/1917 | Eckenrode | 604/353 |
| 3,394,703 | 7/1968 | Orgel | 604/353 |
| 3,489,150 | 1/1970 | Glaude | 604/353 |
| 3,749,096 | 7/1973 | Donaldson | 604/353 |
| 3,999,550 | 12/1976 | Martin | 604/353 |
| 4,387,726 | 6/1983 | Denard | 604/353 |

Primary Examiner—Stephen C. Pellegrino
Assistant Examiner—Michael Rafa
Attorney, Agent, or Firm—Malloy, Downey & Malloy

[57] ABSTRACT

A urinary catheter designed to fit on a male patient including a substantially firm, rigid material cup having an elongated tube for concentric, surrounding relation about the male organ and adjustably attached to the cup for selective positioning of an open proximal end of the tube into and out of a hollow interior portion of the cup and into engagement with the pubic area of the user. A drainage conduit or the like is connected in fluid receiving relation to the distal, exteriorly located end of the tube for removal and collection of urine passing from the patient.

13 Claims, 1 Drawing Sheet

EXTERNAL MALE URINARY CATHETER

BACKGROUND OF THE INVENTION

1. Field of the Invention

This invention relates to a urinary catheter assembly specifically adapted for male patients and including a tube adjustably mounted on a protective cup, both of which engage and at least partially surround the male organ and/or pubic area of the patient to facilitate collection and removal of fluid from the patient to a collection facility.

2. Description of the Prior Art

The prior art is replete with catheter assemblies conventionally termed "external catheters" which are specifically designed for use with a male patient. Such prior art devices would normally have some type of attachment or securement strap, harness, etc. used to attach the catheter to the body of the patient. In addition, a receiving tube normally fits in surrounding, concentric relation to the penis and the aforementioned supporting or attachment straps are used for the support and placement of the receiving tube in an operative position. Such is disclosed in the external male catheter structure of U.S. Pat. No. 3,999,550 to Martin. The receiving catheter tube has its distal end attached to a drainage conduit for removal of the urine to a collection facility or the like. The patent to Komis, U.S. Pat. No. 4,553,968, discloses an external male urinary catheter designed to be used in combination with a garment such as underwear or the like. The catheter assembly comprises a thin flexible, resilient receiving tube disposed in enclosing relation about the penis and having a reinforced end portion forming a contoured, open ended tubular member attached to a drainage tubing communicating with a collection facility.

Yet another structure is disclosed in Komis, U.S. Pat. No. 4,713,066, directed to an external male urinary catheter also associated with a garment, such as underwear wherein a moderately thin flexible, durable receiving sheath is dimensioned to be positioned about the penis. The sheath includes a distal tubular member having a central aperture providing an open end. The difference between the two aforementioned existing patents is in the structure of the receiving tube or catheter member surrounding the penis.

Rothenberg, U.S. Pat. No. 4,713,067, discloses a urinary collection system for male incontinent which primarily relates to a belt having a supporting strap attached to the catheter which fits about the penis substantially similar to a condom and which has a drainage tube attached to the distal end for communicating and directing of the collected fluid to a collection facility.

While each of the above-noted structures existing in the prior art and demonstrated in the above-noted patents are assumed to be operative for their intended function, none have the feature of the receiving catheter tube being adjustable relative to an attachment structure which secures the catheter tube to the patient. Such is important from a practical standpoint in that displacement or natural movement of the patient frequently results in an inadvertent twisting or closing of the catheter tube based on the fact that such tube frequently does not adequately fit the patient's body. Such adjustable features should be present in a preferred structure which enables somewhat lateral movement of the receiving catheter tube relative to the attachment means as well as providing both linear or longitudinal adjustment such that an open proximal end of the receiving catheter tube adequately may fit in sealing engagement about either the penis or generally the base of the penis adjacent the pubic area. In addition, none of the known prior art structures include any type of protective cup serving to better fit and facilitate natural movement of the patient relative to the receiving catheter tube when the catheter assembly is in the preferred operative position.

SUMMARY OF THE INVENTION

The present invention relates to an external male catheter assembly comprising an attachment means in the form of a first supporting belt or strap disposed in adjustably surrounding relation to the waist of the wearer. A cup formed preferably from a substantially firm, at least semi-rigid material has a hollow interior and an open mouth facing inwardly towards the body of the user. The cup is provided in surrounding somewhat enclosing relation to the pubic area and of course, the penis of the patient. A catheter, receiving tube is adjustably and movably secured to the cup by a mounting means which allows both for the longitudinally or linear adjustment of the catheter tube along its length and the lateral displacement of the tube relative to the cup which facilitates natural movement or shifting of the patient without twisting or otherwise displacing the catheter tube.

More specifically, a proximal open end of the tube includes a sealing member about its periphery and is disposed on the interior of the cup in a position to receive placement of the penis of the patient therethrough into the interior of the catheter tube. The distal end of the tube extends outwardly to an exterior of the cup and is connected to a drainage conduit in the conventional fashion. The drainage conduit is provided of course to deliver or channel urine, fluids, etc. to a collection facility which may be strapped or otherwise secured to the patient's leg or other applicable location.

One feature of the present invention is that the catheter tube is adjustable along its length by means of a mounting means secured both to the external surface of the tube and to the periphery of an opening formed in the cup through which the catheter tube passes. This mounting means is even more specifically defined by an externally threaded portion or thread means formed on the external surface of the catheter tube. This threaded portion is specifically configured and disposed to matingly engage the peripheral edge of the periphery of the opening formed in the cup. It should be apparent therefore that rotation of the tube causes adjustable movement of the externally threaded portion relative to the peripheral edge of the opening within the cup. The catheter tube may therefore be adjusted longitudinally to properly position the open distal end relative to the penis which the catheter tube surrounds and encloses.

In one preferred embodiment to be described in greater detail hereinafter, the opening has a preferred elongated or "oblong" configuration. The mating engagement between the outer surface or threaded portion of the catheter tube and the peripheral edge of the periphery of the opening allows for movement of the tube along the length of the elongated opening which facilitates and accommodates the natural "shifting" movement of the patient. Such allowed lateral shifting of the tube relative to the opening and cup will prevent any inadvertent twisting of the catheter tube which could inadvertently render the catheter assembly inoperative by preventing fluid flow from the catheter through the proximal end and into the drainage tube to the aforementioned collection facility.

The catheter tube surrounding the penis is preferably formed from a clear, soft plastic and preferably transparent material. To the contrary, the cup is formed from a firm at least semi-rigid material surrounding the pubic area and penis on a hollow interior portion thereof. A cushioning means is formed around the open periphery of the cup and may be filled with a fluid such a gas, liquid, gel, etc.

In another embodiment to be described in greater detail hereinafter, the attachment means is in the form of a garment to be worn by the patient generally in the configuration of an athletic support in the sense that a surrounding belt has secured in depending relation to a frontal portion thereof a flexible material pouch opening inwardly toward the patient's pubic area. The pouch is dimensioned and configured to receive the cup therein and further includes an aperture disposed in aligned relation to the opening in the front face of the cup. The aperture formed in the pouch allows the protrusion therethrough of the catheter tube as will be apparent hereinafter.

BRIEF DESCRIPTION OF THE DRAWINGS

For a fuller understanding of the nature of the present invention, reference should be had to the following detail description taken in connection with the accompanying drawings in which.

Like reference numerals refer to like parts throughout the several views of the drawings.

DETAILED DESCRIPTION OF THE PREFERRED EMBODIMENT

Figure 1:
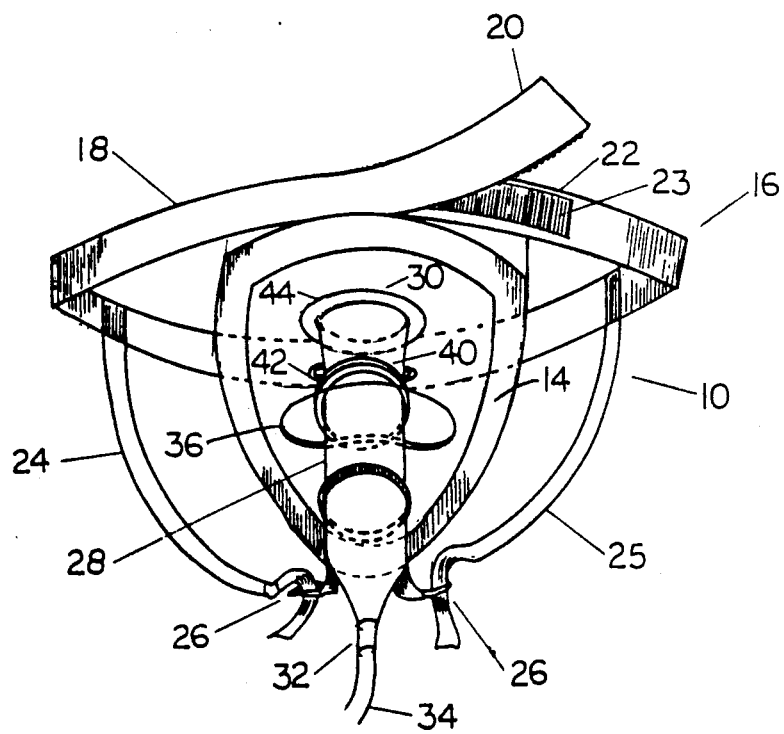
FIG. 1 is a perspective view in partial cut-away of one preferred embodiment of the external catheter assembly of the present invention.

As shown in FIG. 1, the present invention is directed to an external catheter assembly for a male patient and is generally indicated as 10. The assembly comprises a firm, at least semi-rigid material cup 12 having a hollow interior portion sufficient to surround the pubic area and the penis of the male patient. The hollow interior portion of the cup 12 is surrounded by a cushioning means 14 connected to and defining the open periphery of the cup 12. The cushioning means provided of course to supply added comfort to the cup as it is disposed in enclosing relation to the pubic area during the operative positioning of the assembly 10. The cushioning member 14 comprises an elongated chamber filled with air or other fluid to a sufficient degree to provide a soft engagement confronting the skin or other area of the patient. The cup 12 is supported by an attachment means generally indicated as 16 in the form of a first belt or strap 18 disposed and configured to surround generally the waist area of the patient. Opposite ends as at 20 and 22 are free from one another but include connection facilities which may be in the form of a hook and loop type fastener members 23 or any other type of adequate connecting means facilitating the easy and frequent attachment and removal of the opposite ends 20 and 22.

Supporting straps as at 24 and 25 have one end secured to the belt or strap 18 at spaced apart locations to one another and extend downwardly therefrom for removable attachment by any applicable connectors as at 26 to a catheter of receiving tube 28. The receiving tube 28 is adjustably and movably secured to the cup 12 and is preferably formed from a soft, flexible and preferably transparent plastic material. The tube 28 has an open distal end as at 30 disposed on the interior of the cup in receiving relation to the penis of the patient. The opposite or distal end as at 32 is disposed externally of the frontal portion of the cup 12 and is connected to a drainage conduit as at 34 for the channeling of the collected urine or like liquid to a collection facility well known in the art.

An important feature of the present invention is the existence of a mounting means defined by an opening 36 formed in the cup and being of sufficient dimension and configuration to allow the catheter tube 28 to pass therethrough as clearly shown in FIG. 1. In the preferred embodiment shown in FIG. 1, the opening 36 has a somewhat elongated or oblong configuration which allows lateral displacement of the tube along the length of the elongated opening 36 between the opposite ends thereof. This lateral displacement accommodates any natural shifting movement of the patient while wearing the catheter assembly 10 and prevents inadvertent twisting or "closing" of the catheter tube 28 resulting in a backup of the collected urine or fluid rather than having such liquid pass down through the drainage tube 34. The mounting means further comprises an external surface portion as at 40 preferably defined by a thread means or an externally threaded portion 42 cooperatively disposed, structured and configured to cooperate with a peripheral edge 44 of the periphery of the opening 36. Due to the fact that the material from which the cup 12 is formed is at least semi-rigid, rotation of the catheter tube 28 will serve to allow adjustment longitudinally or linearly of the tube along its own length. This in turn will allow selective adjustment and positioning of the open distal end 30 within the interior of the cup so as to accommodate for the different patient sizes and efficiently place the distal open end 30 in a preferred location for reception of the penis to pass therethrough into the interior of the catheter tube 28. It should be apparent therefore that the mounting means is such as to allow both the lateral displacement of the tube along the length of the elongated opening 36 and the linear or longitudinal adjustment of the tube 38 into and out of the cup 12 for preferred placement of the open distal end 30. Other features include a combination seal and cushion member as at 44 which resists leakage of liquid beyond the open distal end 30 as well as providing additional comfort to the wearer when the penis is placed on the interior of the tube 28.

Figure 2:
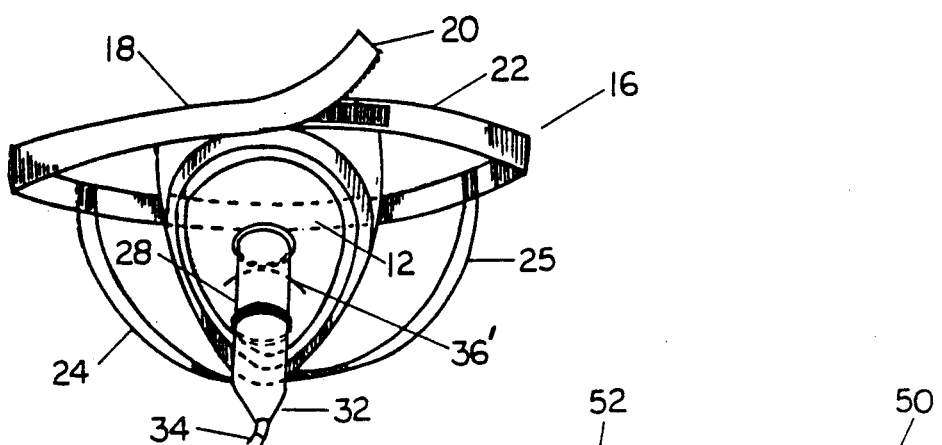
FIG. 2 is a perspective view in partial cut-away of yet another embodiment of the present invention.
Figure 3:
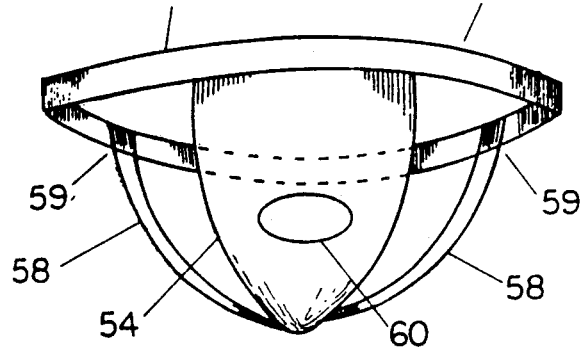
FIG. 3 is a perspective view of another embodiment of the attachment facility which secures the subject catheter assembly to the patient's body.

The embodiment of FIG. 2 differs from the embodiment of FIG. 1 in that the opening 36' is a round or circular opening having a periphery which is dimensioned substantially the same as the outer diameter of the catheter tube 28. In this embodiment, linear adjustment of the catheter tube 28 along its length is possible due to the threaded engagement between the peripheral edge of the opening 36' and the threaded portion 42 formed on the external surface of the tube 28. However, the lateral displacement is prevented since the opening 36' is substantially the same configuration and dimension as is the tube 28.

Yet another embodiment of the present invention is the provision of an attachment means generally indicated as 50 generally in the form of an athletic supported type garment to be worn by the patient. The attachment means 50 and/or garment is more specifically defined by a surrounding belt 52 disposed about the waist of the wearer and further including a depending supported pouch as at 54 formed from a flexible material. The pouch 54 is further dimensioned and configured to receive and support the rigid material cup 12 on the interior thereof so as to position the cup in operative relation to the pubic area and penis of the patient. Supporting leg straps as at 58 have their upper ends as at 59 secured to the belt 52 and their lower ends secured to the bottom or lower most portion of the pouch 54. Further, the pouch 54 includes an aperture 60 intended to be disposed in aligned relation with either the opening 36 (see FIG. 1) or the opening 36' (see FIG. 2) to allow for the passage of the catheter tube 28 to pass therethrough. The pouch 54 is thereby disposed, structured and configured to provide support and securement of the cup 12 in its operative position relative to the patient.

Now that the invention has been described, what is claimed is:

1. An external male urinary catheter assembly comprising:
   (a) a cup formed of a firm, substantially rigid material and including a substantially hollow interior portion dimensioned and configured to surround the pubic region of the user's body and receive the male organ therein,
   (b) an elongated tube removably secured to said cup intermediate opposite end thereof and including an open proximal end, said proximal end extending into said hollow interior of said cup, a distal end extending outwardly from said hollow interior portion and having a drainage conduit attached thereto,
   (c) said tube dimensioned to receive the male organ therein in outer, surrounding relation thereto, said distal end and drainage tube attached thereto being disposed in fluid receiving relation to the male organ,
   (d) attachment means connecting to and extending from said cup for securing the assembly in an operative position to the user's body, and
   (e) a mounting means formed on both said cup and said tube including an opening formed in said cup being dimensioned to receive said tube therethrough for adjustably positioning the tube along its length relative to said cup.

2. An assembly as in claim 1 further comprising cushioning means formed along an open periphery of said cup and disposed in engaging relation to the pubic area and surrounding the male organ for comfortably fitting the cup on the body of the user.

3. An assembly as in claim 2 wherein said cushioning means comprises a fluid containing chamber disposed substantially continuously about the open periphery.

4. An assembly as in claim 3 wherein said mounting means comprises said opening formed in said cup and dimensioned to receive said tube therein, an outer periphery of said opening movably engaging an outer surface of said tube.

5. An assembly as in claim 4 wherein said outer surface of said tube is structured to matingly engage said outer periphery and said opening and is adjustable, linearly into and out of said cup upon the movement of said outer surface relative to said outer periphery.

6. An assembly as in claim 5 wherein said outer surface is structured and configured to rotatably engage an exposed peripheral edge of said outer periphery of said opening.

7. An assembly as in claim 6 wherein said outer surface comprises thread means rotatably and matingly engaging said outer periphery for linear adjustability of said tube into and out of said cup upon rotation of said thread means relative to and in engagement with said peripheral edge.

8. An assembly as in claim 7 wherein said opening comprises an elongated configuration, said tube movably laterally along the length of said opening.

9. An assembly as in claim 4 wherein said opening comprises an elongated configuration, said tube movable laterally along the length of said opening.

10. An assembly as in claim 9 wherein said open proximal end includes a seal means formed about a periphery thereof for sealing engagement of said proximal end relative to said pubic area in surrounding relation to the male organ.

11. An assembly as in claim 1 wherein said attachment means comprises a first strap adjustably positioned around the waist of the wearer and a plurality of support straps depending downwardly therefrom in attaching support to said cup.

12. An assembly as in claim 11 wherein said first strap is adjustably secured about the waist of the user, whereby the dimension of the user may be accommodated for by adjustment of said first strap.

13. An assembly as in claim 1 wherein said attachment means comprises a first belt disposed in surrounding relation to the waist of the wearer, a flexible material pouch depending from a frontal portion of said belt downwardly in overlying relation to the pubic area and male organ to a point beneath the legs of the user, said pouch dimensioned and configured for supporting reception of the cup therein, said pouch including an aperture for accommodation of said tube to pass through both said pouch and into engagement with said cup.

* * * * *